United States Patent [19]
Buck et al.

[11] Patent Number: 6,104,487
[45] Date of Patent: Aug. 15, 2000

[54] PLASMA ETCHING WITH FAST ENDPOINT DETECTOR

[75] Inventors: David Wallace Buck, Mesquite; Gabriel G. Barna, Richardson, both of Tex.

[73] Assignee: Texas Instruments Incorporated, Dallas, Tex.

[21] Appl. No.: 08/989,607

[22] Filed: Dec. 12, 1997

Related U.S. Application Data

[60] Provisional application No. 60/033,564, Dec. 20, 1996.

[51] Int. Cl.[7] .................. G01L 21/30; G01J 3/443; G01J 3/30
[52] U.S. Cl. .................. 356/316; 356/311; 216/60
[58] Field of Search .................. 216/60; 356/311, 356/316

[56] References Cited

U.S. PATENT DOCUMENTS

| | | | |
|---|---|---|---|
| 4,611,919 | 9/1986 | Brooks, Jr. et al. | 216/60 |
| 4,690,558 | 9/1987 | Tsunoyama et al. | 356/318 |
| 4,846,920 | 7/1989 | Keller et al. | 216/60 |
| 5,298,466 | 3/1994 | Brasseur | 437/228 |
| 5,320,704 | 6/1994 | Horioka et al. | 216/60 |
| 5,352,902 | 10/1994 | Aoki | 250/575 |
| 5,565,114 | 10/1996 | Saito et al. | 216/60 |
| 5,728,253 | 3/1998 | Saito et al. | 216/60 |
| 5,759,424 | 5/1998 | Imatake et al. | 216/60 |

Primary Examiner—Frank G. Font
Assistant Examiner—Zandra V. Smith
Attorney, Agent, or Firm—Mark A. Valetti; Carlton H. Hoel; Frederick J. Telecky, Jr.

[57] ABSTRACT

A system and process for analyzing the plasma discharge for various frequency components that can be correlated to wafer, chamber or equipment conditions. This system and process monitors (step 210), by using optical or electrical signals from the plasma, the low frequency plasma variations (step 220) generated during the wafer manufacturing process. For example, in endpoint detection applications, the amplitude variations of the plasma glow at a selected audio frequency, chosen for sensitivity to the etched material, is used to generate the endpoint signal (step 230). This endpoint signal has a potential response time equal to one cycle of the selected frequency plus minimal filtering due to noise reduction. To extract the vital parameters from the plasma glow, DSPs for frequency analysis or simple frequency filtering methods can be used.

13 Claims, 2 Drawing Sheets

PLASMA ETCHING WITH FAST ENDPOINT DETECTOR

This is a Non Provisional application filed under 35 USC 119(e) and claims priority of prior provisional, Ser. No. 60/033,564 of inventor Buck, et al, filed Dec. 20, 1996.

BACKGROUND AND SUMMARY OF THE INVENTION

The present invention relates to plasma diagnostics in integrated circuit processing.

Plasma etching is a fundamental and widely used technique in integrated circuit fabrication. In the simplest case a wafer is mounted on a ground electrode, and RF power is applied to another electrode which is parallel to the wafer, while a gas containing a species which contains a reactive element is flowed past the wafer. (For example, $CF_4$ is a source of fluorine, and $Cl_2$ is a source of chlorine.) The electrical excitation in the plasma volume will dissociate the source gasses to produce very reactive species.

Many variations of plasma etching can be distinguished (such as reactive ion etching, reactive sputter etching, ECR etching, and pre-excited etching), but all share the feature that RF power is used to create highly active chemical species in close proximity to the wafer (usually using a plasma at the wafer surface, to provide bombardment).

A basic requirement of plasma etching is endpoint detection. There are enough variations in thin film thickness and composition that it is highly desirable to know when an etching step is complete. This is usually done by an "endpoint detection" process, which senses the changes in the plasma chemistry when new layers are exposed. For example, during a metal etch the underlying dielectric will first be exposed when the etch has gone through the thinnest part of the metal, and some etch products from the dielectric may then appear in the plasma. As more of the dielectric is exposed, more of these etch products may appear in the plasma. When the pattern in the metal layer has been etched completely, the shift in the plasma chemistry will essentially stop.

Thus there is a great need for plasma sensors to detect such shifts in plasma chemistry. Plasma sensors are needed not only for endpoint detection, but also for hardware and process diagnostics and control of semiconductor manufacturing equipment.

The simplest plasma endpoint sensors simply look for a particular spectral line, usually at ultraviolet or short visible wavelengths. For example, when aluminum is exposed to a plasma etch process some aluminum will be present in the plasma, and the plasma will radiate at 261 nm; when aluminum is not present, radiation at this wavelength will be much weaker.

However, this conventional technique has some significant problems: one is degradation of the windows in the plasma reactor. A plasma generates very reactive chemical species, so the windows of the plasma reactor rapidly become cloudy due to etching or deposition on their interior surfaces. This cloudiness is particularly bad at shorter wavelengths (blue and ultraviolet). A second problem is the required filtering: the optical input at the wavelength being monitored is typically filtered with a time constant of the order of one second, which delays the eventual endpoint detection.

Some previous approaches to endpoint detection are shown in the following literature, all of which is hereby incorporated by reference: Griffiths and Degenkolb, 31 Appl. Spectrosc. 134 (1977); Angell and Oehrlein, "Grazing angle optical emission interferometry for end-point detection," 58 Appl. Phys. Lett. 240 (1981); Sternheim and voln Gelder, "A Laser Interferometer System to Monitor Dry Etching of Patterned Silicon," 130 J. Electrochem. Soc. 655 (1983); Kolodner et al., "End-point detection and etch-rate measurement during reactive-ion etching using fluorescent polymer films," 1 J. Vac. Sci. Tecnol. 501 (1983); Weiss, "Endpoint Monitors," Semiconductor International, September 1988, page 98.

PLASMA MONITORING SYSTEMS AND METHODS

The present inventors have discovered an innovative system and process for analyzing the plasma discharge. This system monitors, by using optical or electrical signals from the plasma, the low frequency plasma variations generated during the wafer manufacturing process. This is a novel approach to looking at plasma process information. One important use of this technique is for endpoint detection. In such applications the amplitude variations of the plasma at a selected frequency are used as the endpoint-detection (EPD) signal. This EPD signal has a potential response time equal to one cycle of the selected frequency plus minimal filtering due to noise reduction. To extract the vital parameters from the plasma glow, frequency analysis using digital signal processors (DSPs) or simple frequency filtering methods can be used. The filtering operation extracts frequency components which give information about changes in wafer, chamber or equipment conditions.

The advantages provided by this innovative system and process include:

ability to examine a wide range of frequencies generated in the plasma discharge;

opens a new dimension for plasma diagnostics;

in endpoint detection applications, ability to indicate endpoint conditions at a faster rate (e.g. at least two seconds);

produces signal using visible component of plasma light; and shows little signal degradation over time.

BRIEF DESCRIPTION OF THE DRAWING

The disclosed inventions will be described with reference to the accompanying drawings, which show important sample embodiments of the invention and which are incorporated in the specification hereof by reference, wherein.

DETAILED DESCRIPTION OF THE PREFERRED EMBODIMENTS

The numerous innovative teachings of the present application will be described with particular reference to the presently preferred embodiment. However, it should be understood that this class of embodiments provides only a few examples of the many advantageous uses of the innovative teachings herein. In general, statements made in the specification of the present application do not necessarily delimit any of the various claimed inventions. Moreover, some statements may apply to some inventive features but not to others.

Figure 1:
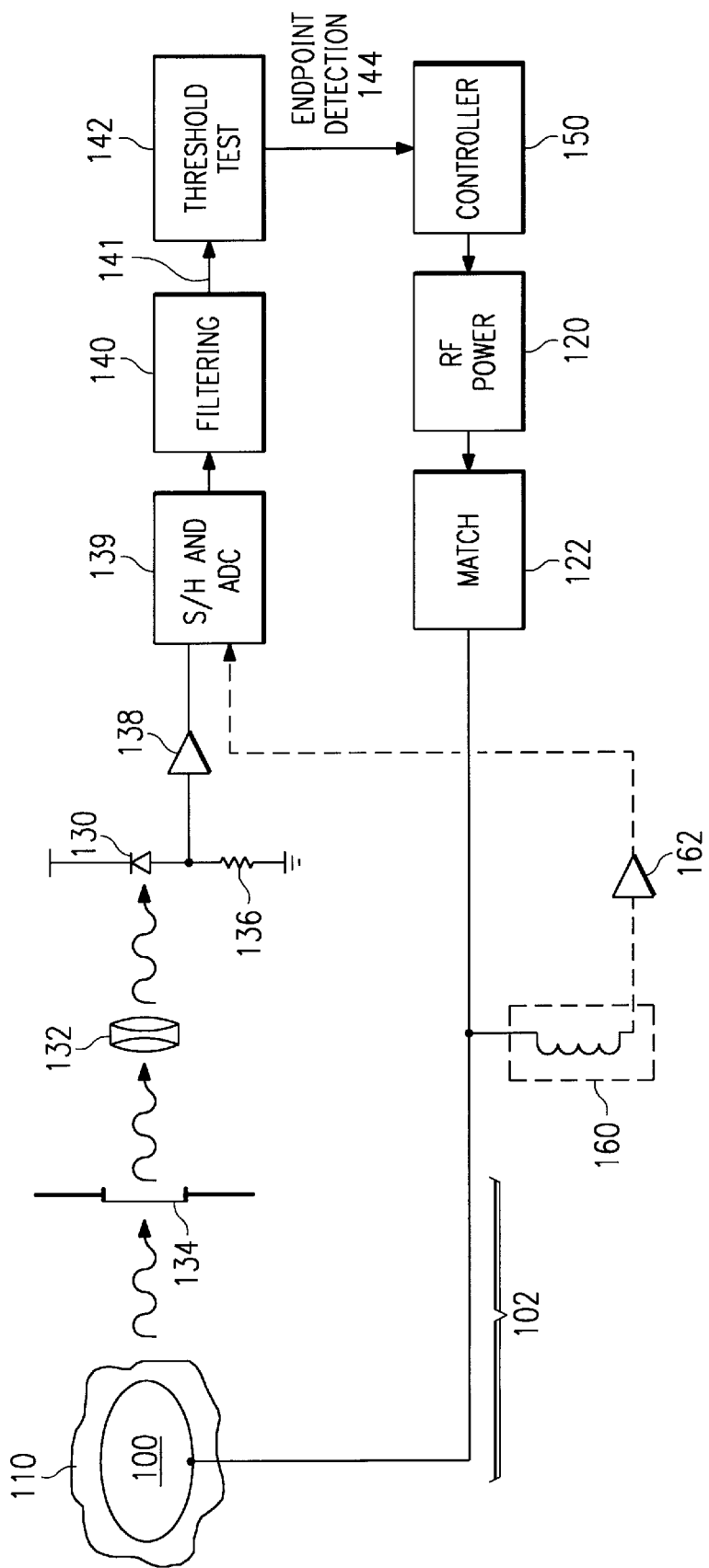
FIG. 1 shows a sample system utilizing the plasma monitoring methods of the present invention.

FIG. 1 shows a sample system implementation. A plasma reactor 102 is shown only very schematically, to emphasize the portions most relevant to the disclosed inventions. (In practice, the wafer 100 would be supported by a cooled susceptor, and the RF power might be connected through the susceptor or to a parallel plate which is spaced apart from the wafer.) A plasma 110 is generated in the low-pressure gasses near the surface of the wafer 100, by RF power from RF power stage 120 (applied through an impedance-matching network 122). A broad-band photodetector 130 looks at the plasma glow 110 through an (optional) optical train 132 (and a window 134 which is set in a port of the reactor 102). (In this example the photodetector 130 is shown as a photodiode with a simple load 136, but of course various other electro-optical configurations can be used instead. The diode itself, in this embodiment, is a common infraredsensitive diode with a peak in 900 nm range, and sensitivity over a wide range of infrared and visible wavelengths.) A following amplifier stage 138 and sampling converter stage 139 provide a digital data output at an 11 KHz sampling rate.

Analysis of this optical intensity data, in the 100 to 5000 Hz range, has shown the presence of several frequency components that appeared and disappeared during the plasma process. These frequency components provide information about the plasma operation, showing for example the aluminum period of the wafer etch. There are many low frequencies from just above DC to just under the plasma RF generator frequency that contain important information about the plasma, the wafer or the machine.

Thus in the configuration of FIG. 1 the digital data output is subjected to a filtering operation 140 to extract one or more low-frequency components 141 of the variation in the plasma intensity, and a threshold test operation 142 provides an endpoint detection output 144 which is dependent on the low-frequency component 141. A controller 150 uses this signal 144 to continue etching for only the desired period of overetch, and then turns off the RF power stage 120 and initiates the process of unloading the wafer.

Figure 3:
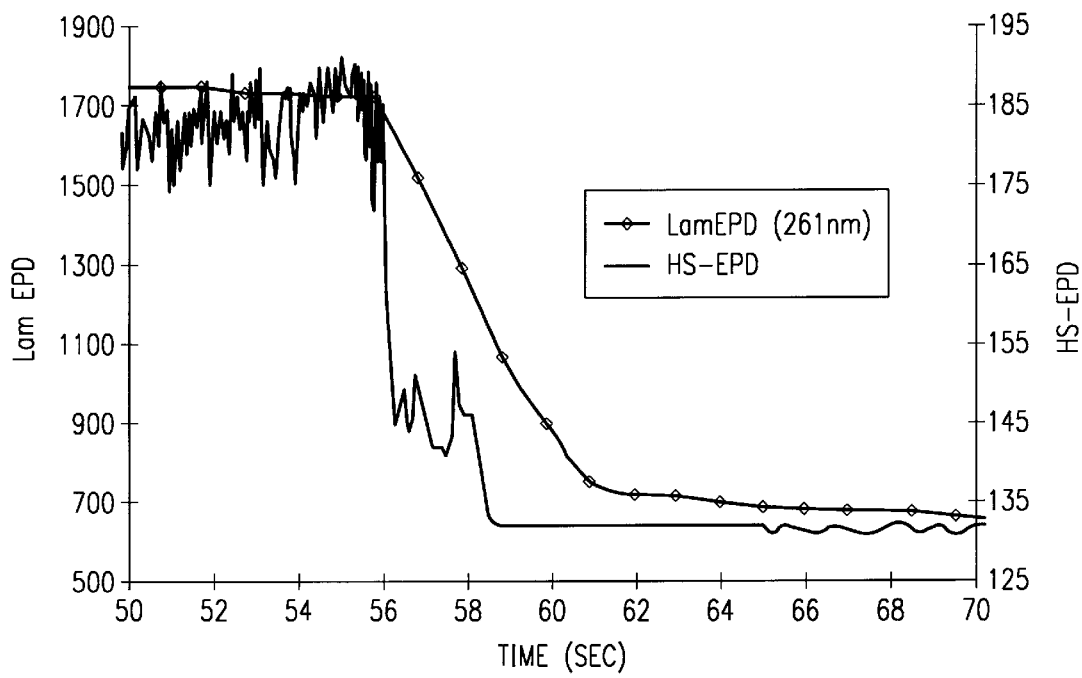
FIG. 3 compares the Al endpoint detection outputs of a conventional endpoint detector with that of the endpoint detector of the present invention.

The plot of FIG. 3 shows that a simple comparison with a threshold value would provide an adequate endpoint detection algorithm in this case. Such a threshold test operation 142 is of course only a very simple example of a decision algorithm, but a wide variety of other decision algorithms can be used instead. Regardless of what decision algorithm is used, the present invention provides a new source of information which can be used in the decision algorithm to improve results.

Preferably the filtering operation 140 and thresholding operation 142 are combined in a single programmable digital signal processor (DSP) chip, but alternatively a microprocessor can be used for this instead. Optionally the controller 150 is also implemented in the same hardware.

Optionally the energy seen at the target frequency can be normalized to the total output from the photodiode, to eliminate effects due to window clouding, variation in photodiode position, etc., or alternatively a ratio of spectral components can be monitored.

By using optics 132 which see only a narrow field of view, and directing these optics at the plasma near the wafer surface, the inventors have discovered that the variation in the plasma brightness is stronger near the wafer surface. This suggests that the oscillation in the plasma may be due to loading effects.

Figure 2:
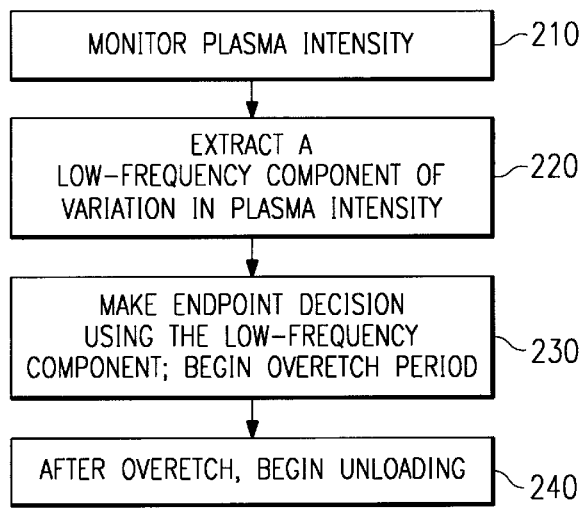
FIG. 2 shows a flowchart for endpoint detection as disclosed in the present application.

FIG. 2 shows a flowchart for endpoint detection as disclosed in the present application. The luminosity of the plasma is measured (step 210), and specific low frequencies (230 Hz for example) are filtered (step 220) to produce an endpoint trace with data rates that are extremely fast relative to the process times. (The frequencies which are monitored can be changed, for different processes, to optimize sensitivity to the material being etched.) When the endpoint is thus detected, the controller can initiate overetch if desired (step 230) and unloading (step 240). Use of the low-frequency variation provides much more information about the process change during the "endpoint" period. This technique is more tolerant of the window clouding problem because the optical input is via a broad-band photodetector which enables the window clouding problem to have a lesser effect.

Tests indicate that the disclosed endpoint detector indicates an endpoint condition about two seconds faster than the present Lam 9600 EPD. In addition, the disclosed endpoint detector produces this signal by using the visible components of the plasma light (e.g. greater than 500 nm), while the Lam 9600 EPD uses 261 nm. The 261 nm UV region is several orders of magnitude more susceptible to window clouding than the visible region, therefore, the disclosed endpoint detector will show minimal signal degradation over time.

FIG. 3 compares the A1 endpoint spectrums of the present LAM 9600 EPD and the high-speed endpoint detector of the present invention. A 230 Hz signal, occurring during the A1 etching of an TiN/A1/TiN/oxide stack on a Lam 9600 TCP reactor, was observed using the high-speed endpoint detector of the preferred embodiment of the present invention. Note that the high-speed endpoint detector provides a much faster transition when the endpoint is reached.

In this experiment, the etch operation was etching 1 micron of TiN over aluminum, at a pressure of 12 milliTorr, at a susceptor temperature of 30 degrees C, with flows of 30 sccm of chlorine and 75 sccm of BC13, and RF power of 350 Watts transformer-coupled into the plasma plus 135 Watts RF bias power. A photodetector was pointed at the plasma near the wafer surface, and the 230 Hz component of luminosity variation was extracted. For comparison, a conventional optical endpoint detection was performed by detecting ultraviolet light at wavelengths near 261 nm.

After the endpoint was detected, the etch is continued for a specified time, to get the desired degree of overetching.

Alternative Embodiment without Optical Train

Optionally the lens 132 can be omitted, and the photodetector 130 can simply be pointed at the plasma. This has been experimentally tested, and found to give a good indication of the endpoint transition.

Alternative Embodiment Using Infrasonic Frequencies

In the presently preferred system embodiment, two separate RF power connections are used, at frequencies which are separated by about 1000 Hz. Thus a beat frequency component (1000 Hz) appears in the spectrum. The lines which are preferably monitored are below 1000 Hz, but varying components were also seen at frequencies of up to several KHz. Thus in principal frequencies above 1000 Hz can be used instead, although frequencies below 1000 Hz are preferred.

The amplifier used in the successful experimental results described herein had a bandwidth of approximately 100 Hz–10,000 Hz. Thus luminosity variation at lower frequencies was not fully measured in this experiment. However, it is known that luminosity variation occurs at frequencies down to about 10 Hz, since visible flickering can be observed, and it is contemplated that monitoring of sub-100 Hz frequencies can also usefully provide information about the plasma.

Of course the frequencies monitored should not include power-line frequencies or their low harmonics, or at least should be filtered to exclude such components.

Alternative Embodiment with Electrical Monitoring

In alternative embodiments, the electrical connections can be monitored to monitor low-frequency oscillations. The connections to the RP drive often include capacitive elements in the matching networks, but of course an inductor can be used to provide a low-pass connection for detection of low-frequency variations in the electrical characteristics of the plasma.

FIG. 1 shows these connections as an optional modification. A low-pass filter 160 is coupled to the RF bias connection, without any intervening matching stage 122. (The matching stages 122 are normally optimized for the RF frequency, and tend to filter out the low-frequency information which is measured by the present invention.) An audio-frequency amplifier 162 then provides an analog input to the sampling converter 139 (which in this embodiment is connected to amplifier 162 and not to amplifier 138), and signal-processing and control decisions are performed accordingly by stages 140, 142, and 150.

Alternative Embodiment with Electrical and Optical Monitoring

In this alternative embodiment a two-channel sampling converter 139 is used, and the filtering operation 140 operates on two channels of input. (Optionally the filtering operation 140 can include some correlation operations, to provide an output which is dependent on both channels of input.) Thus in this embodiment the sampling converter 139 is connected both to amplifier 162 and also to amplifier 138.) Control decisions are performed accordingly by stages 140, 142, and 150.

Alternative Embodiment Using Power Ratios

In one class of alternative embodiments, it is contemplated that the ratio of two low-frequency components can be used as the endpoint indicator. This embodiment is expected to be particularly advantageous, since the ratio of two frequency components is expected to provide greater noise immunity).

Alternative Embodiment Using Optical Filtering Plus Low-Frequency Extraction

In another class of alternative embodiments, conventional optical filtering can be using in combination with the low-frequency extraction methods described above. Thus in this embodiment the low-frequency extraction methods would be performed on a raw signal which is derived from narrowband optics rather than from broadband optics. This embodiment is not presently preferred, but does provide another way to exploit the innovative teachings of the present application.

According to a disclosed class of innovative embodiments, there is provided: A system for analyzing a plasma discharge, comprising: a photodetector optically coupled to monitor the intensity of light emission from at least one portion of the plasma discharge, said photodetector providing a corresponding electrical output; and at least one filter connected to receive said electrical output and monitor therein amplitude variations at at least one audio frequency, and provide an output which is dependent on said amplitude variations.

According to another disclosed class of innovative embodiments, there is provided: A plasma reactor system, comprising: a chamber which encloses a wafer support; at least one electrode positioned to generate a plasma discharge in proximity to said wafer support, when RF power is applied to said electrode; a photodetector optically coupled to monitor the intensity of light emission from at least one portion of said plasma discharge, said photodetector providing a corresponding electrical output; and at least one filter connected to receive said electrical output and monitor therein amplitude variations at at least one audio frequency, and provide an output which is dependent on said amplitude variations.

According to another disclosed class of innovative embodiments, there is provided: A method for plasma etching, comprising the steps of: plasma etching a wafer; and monitoring audio-frequency variation in the plasma intensity during said etching step; and discontinuing said etching step at a time which is dependent on said monitoring step.

Modifications and Variations

As will be recognized by those skilled in the art, the innovative concepts described in the present application can be modified and varied over a tremendous range of applications, and accordingly the scope of patented subject matter is not limited by any of the specific exemplary teachings given.

It should also be noted that the disclosed plasma monitoring techniques do not have to be used to detect only a single transition in plasma characteristics, but can be used to track multiple transitions as multiple new layers are exposed (or as old layers disappear).

It is also possible to monitor the relations between three or more frequencies in the plasma brightness, to get a more accurate indicate of a particular transition.

What is claimed is:

1. A method for plasma etching, comprising the steps of:
   (a.) plasma etching a wafer; and
   (b.) monitoring audio-frequency or infrasonic variation in the plasma intensity during said etching step; and
   (c.) discontinuing said etching step (a.) at a time which is dependent on said monitoring step (b.).

2. The method of claim 1, wherein said monitoring step uses a photodiode having a peak sensitivity in the infrared to detect variations in broadband optical emission from the plasma.

3. The method of claim 1, wherein said monitoring step uses an electrical connection to detect variations in RF voltage or current.

4. A system for analyzing a plasma discharge, comprising:
   a photodetector optically coupled to monitor the intensity of light emission from at least one portion of the plasma discharge, said photodetector providing a corresponding electrical output; and
   at least one filter connected to receive said electrical output and monitor therein amplitude variations at at least one audio frequency, and provide an output which is dependent on said amplitude variations.

5. The system of claim 4, wherein said filter is a digital signal processor or bandpass filter.

6. The system of claim 4, wherein said at least one portion of the plasma discharge is directly adjacent to the wafer surface.

7. The system of claim 4, wherein said photodetector is optically coupled to monitor the intensity of light emission over a range of wavelengths which includes at least 400 nm of difference between maximum and minimum wavelengths.

8. The system of claim 4, wherein said photodetector is a photodiode having a peak sensitivity in the infrared.

9. A plasma reactor system, comprising:
   a chamber which encloses a wafer support;
   at least one electrode positioned to generate a plasma discharge in proximity to said wafer support, when RF power is applied to said electrode;

a photodetector optically coupled to monitor the intensity of light emission from at least one portion of said plasma discharge, said photodetector providing a corresponding electrical output; and at least one filter connected to receive said electrical output and monitor therein amplitude variations at at least one audio frequency, and provide an output which is dependent on said amplitude variations.

10. The system of claim 9, wherein said filter is a digital signal processor or bandpass filter.

11. The system of claim 9, wherein said at least one portion of the plasma discharge is directly adjacent to the wafer surface.

12. The system of claim 9, wherein said photodetector is optically coupled to monitor the intensity of light emission over a range of wavelengths which includes at least 400 nm of difference between maximum and minimum wavelengths.

13. The system of claim 9, wherein said photodetector is a photodiode having a peak sensitivity in the infrared.

* * * * *